United States Patent
Taeschler et al.

(10) Patent No.: US 10,968,187 B2
(45) Date of Patent: Apr. 6, 2021

(54) METHOD FOR PREPARATION OF ALKYLATED OR FLUORO, CHLORO AND FLUOROCHLORO ALKYLATED COMPOUNDS BY HETEROGENEOUS COBALT CATALYSIS

(71) Applicant: Lonza Ltd, Visp (CH)

(72) Inventors: Christoph Taeschler, Visp (CH); Florencio Zaragoza Doerwald, Visp (CH); Stefan Ellinger, Visp (CH); Matthias Beller, Nienhagen (DE); Helfried Neumann, Rostock (DE); Florian Fischer, Rostock (DE)

(73) Assignee: Lonza Solutions AG, Visp (CH)

( * ) Notice: Subject to any disclaimer, the term of this patent is extended or adjusted under 35 U.S.C. 154(b) by 0 days.

(21) Appl. No.: 16/632,572

(22) PCT Filed: Jul. 26, 2018

(86) PCT No.: PCT/EP2018/070242
§ 371 (c)(1),
(2) Date: Jan. 21, 2020

(87) PCT Pub. No.: WO2019/020726
PCT Pub. Date: Jan. 31, 2019

(65) Prior Publication Data
US 2020/0157063 A1    May 21, 2020

Related U.S. Application Data

(60) Provisional application No. 62/540,656, filed on Aug. 3, 2017.

(30) Foreign Application Priority Data

Jul. 28, 2017  (EP) ..................... 17020321
May 18, 2018  (EP) ..................... 18173211
Jun. 26, 2018  (EP) ..................... 18179739

(51) Int. Cl.
*C07D 265/30* (2006.01)
*B01J 31/04* (2006.01)
*C07C 17/275* (2006.01)
*C07C 17/32* (2006.01)
*C07C 21/18* (2006.01)
*C07D 213/26* (2006.01)
*C07D 241/10* (2006.01)
*C07D 333/12* (2006.01)
*C07D 473/10* (2006.01)
*C07C 19/14* (2006.01)
*C07C 22/08* (2006.01)
*C07C 23/36* (2006.01)

(52) U.S. Cl.
CPC ............ *C07D 265/30* (2013.01); *B01J 31/04* (2013.01); *C07C 17/275* (2013.01); *C07C 17/32* (2013.01); *C07C 21/18* (2013.01); *C07D 213/26* (2013.01); *C07D 241/10* (2013.01); *C07D 333/12* (2013.01); *C07D 473/10* (2013.01); *B01J 2531/845* (2013.01); *C07C 19/14* (2013.01); *C07C 22/08* (2013.01); *C07C 23/36* (2013.01)

(58) Field of Classification Search
CPC .................................................. C07D 265/30
See application file for complete search history.

(56) References Cited

U.S. PATENT DOCUMENTS 9,809,596 B1    11/2017  Taeschler et al.
2017/0158695 A1  6/2017  Taeschler et al.

FOREIGN PATENT DOCUMENTS

WO    WO9316969    9/1993

OTHER PUBLICATIONS

International Search Report and Written Opinion for PCT/EP2018/070242 dated Sep. 24, 2018, 9 pages.

*Primary Examiner* — Paul V Ward
(74) *Attorney, Agent, or Firm* — Dority & Manning, P.A.

(57) ABSTRACT

The invention discloses a method for preparation of alkylated, fluoro alkylated, chloro alkylated and fluorochloro alkylated compounds by a heterogeneous Co-catalysed alkylation or fluoro, chloro and fluorochloro alkylation with alkyl halides, fluoro alkyl halides, chloro alkyl halides or fluorochloro alkyl halides respectively.

11 Claims, No Drawings

METHOD FOR PREPARATION OF ALKYLATED OR FLUORO, CHLORO AND FLUOROCHLORO ALKYLATED COMPOUNDS BY HETEROGENEOUS COBALT CATALYSIS

CROSS REFERENCE TO RELATED APPLICATIONS

This application is the U.S. National Stage entry of International Application Number PCT/EP2018/070242 filed under the Patent Cooperation Treaty having a filing date of Jul. 26, 2018, which claims priority to European Patent Application No. 17020321.0 having a filing date of Jul. 28, 2017, European Patent Application No. 18173211.6 having a filing date of May 18, 2018, European Patent Application No. 18179739.0 having a filing date of Jun. 26, 2018, and U.S. Patent App. No. 62/540,656 having a filing date of Aug. 3, 2017, which are incorporated herein by reference.

The invention discloses a method for preparation of alkylated, fluoro alkylated, chloro alkylated and fluorochloro alkylated compounds by a heterogeneous Co-catalysed alkylation or fluoro, chloro and fluorochloro alkylation with alkyl halides, fluoro alkyl halides, chloro alkyl halides or fluorochloro alkyl halides respectively.

BACKGROUND OF THE INVENTION

Organofluorine chemistry plays an important role in medicinal, agricultural, and material sciences and fields. Haloalkyl groups have strong effects on the properties of compounds such as stability and lipophilicity, and in addition, long chain haloalkyl groups, in particular fluoroalkyl groups provide high water- and oil-resistance and low friction.

There have been various approaches to provide alkylated or haloalkylated compounds by homogeneous catalysis. However homogeneous catalysis suffers from the inherent problems associated with homogeneous catalyzed reactions due to the use of unrecoverable catalysts comprising metals and ligands. In particular inconveniences with regard to catalyst handling, recyclability, and separation of the catalyst from products, impede the transfer of these approaches to large-scale industrial processes. Furthermore expensive and structurally complicated ligands are required in homogeneous catalysis, which are often not commercially available for use on industrial scale.

EP 0 114 359 A1 discloses a process for the manufacture of perfluoroalkyl substituted carbocyclic or heterocyclic compounds by reaction of perfluoroalkyl iodides with unsubstituted or substituted carbocyclic or heterocyclic compounds at elevated temperatures and in presence of at least one alkaline salt, characterized by carrying out the reaction in the presence of at least one metal of the first or eight auxiliary group of the periodic table or in the presence of a complex compound containing said metal as the central atom.

WO 93/16969 A discloses a process for the catalytic perfluoroalkylation of aromatic compounds, wherein a perfluoroalkyl iodide or mixture of iodides is reacted with an aromatic compound in the presence of an aqueous base, such as an alkali metal hydroxide or carbonate, and discloses that further improvements in rate and yield are secured by employing, as the catalyst, a noble metal supported on porous silica microspheres.

EP 1 947 092 A1 discloses perfluoroalkylation of nucleobases with a perfluoroalkyl halide in the presence of a sulfoxide, a peroxide and an iron compound. A specifically mentioned catalytic system is a $Fe_2(SO_4)_3/H_2SO_4/H_2O_2$ system.

WO 2015/185677 A1 describes a method for preparation of alkylated or fluoro, chloro and fluorochloro alkylated compounds by heterogeneous catalysis using a Pt/C-catalyst in the presence of $Cs_2CO_3$ or $CsHCO_3$. While the use of a Pt/C-catalyst allows for heterogeneous catalysis, Pt is an expensive metal resulting in considerable costs for the manufacturing process of alkylated or haloalkylated compounds on an industrial scale.

Therefore there was a need for a heterogeneously catalyzed process for the preparation of alkylated or haloalkylated and in particular of perfluoroalkylated compounds, which provides high yields. The method should be applicable to a wide variety of substrates and should be compatible with a wide variety of functional groups. Furthermore the method should not be restricted to iodides as alkylating agent only, but should also work with other halides in particular with bromides. And the method should work not only with perfluorinated alkyl halides, but also with fluorinated and chlorinated alkyl halides. Furthermore, since noble metal catalysts used so far are expensive, a catalyst system which works effectively without noble metal is desired.

Surprisingly, these requirements could be achieved by the method according to the present invention, which uses as catalyst, herein also called CAT, also abbreviated with Co-L1/C, a cobalt 1,10-phenanthroline supported on carbon, L1 is 1,10-phenanthroline. Co-L1/C and its preparation is described in Westerhaus et al., Nature Chemistry, 2013, 5, 537-543, especially in FIG. 1 therein, and in the supplementary information to this article, available under DOI: 10.1038/NCHEM.1645, under chapter "S1. Catalyst preparation".

According to the present invention a substrate, herein also called COMPSUBST, is reacted in the presence of CAT with a halide, the alkylating agent, herein also called ALKHAL, to introduce an alkyl, fluoro alkyl, chloro alkyl or fluorochloro alkyl residue into COMPSUBST and thereby forming the product which is an alkylated, fluoro alkylated, chloro alkylated or fluorochloro alkylated compound, herein also called ALKYLCOMPSUBST.

The use of Co-L1/C as catalyst provides unexpected advantages. In particular the catalyst can be reused and is not deactivated by the reaction.

The method is applicable both to aromatic and non-aromatic compounds. Also heterocyclic compounds can be converted, even nonactivated thiophenes react smoothly at comparably low temperatures.

A particular advantage of the method according to the invention is that not only iodides can be used as alkylating agent, that is as ALKHAL, but that also good results are obtained with bromides as alkylating agent. It was surprisingly found that also when using bromides as ALKHAL high selectivites and high yields were obtained, also with different substrates, by use of the catalyst Co-L1/C. This has essential advantages in practice as the bromides are significantly more favorable compared to the iodides and therefore the method can be carried out much more efficiently. Further, side products emerging from the use of iodides are more difficult to dispose.

Further, due to the use of a cobalt containing catalyst instead of a nobel metal catalyst, considerable cost savings are achieved.

In this text, the following meanings are used, if not otherwise stated:

alkyl linear or branched alkyl; preferably linear alkyl;

"any of the" is used synonymously with "at each occurrence", for example "any of the R24, R34, R28 and R38 are identical or different and independently from each other selected from the group consisting of" is used synonymously with "R24, R34, R28 and R38 at each occurrence are identical or different and independently from each other selected from the group consisting of"

DBU 1,8-diazabicyclo[5.4.0]undec-7-en;

halide $F^-$, $Cl^-$, $Br^-$ or $I^-$; preferably $Cl^-$, $Br^-$, and $I^-$; more preferably $Br^-$ and $I^-$; even more preferably $Br^-$;

halogen or halo F, Cl, Br or I; preferably F, Cl or Br; more preferably F or Cl;

HRMS EI High Resolution Mass Spectrometry Electron Impact;

"linear" and "n-" are used synonymously with respect to the respective isomers of alkanes;

L1 1,10-phenanthroline;

Co-L1/C cobalt 1,10-phenanthroline supported on carbon, to be more precise it is cobalt oxide supported on 1,10-phenanthroline/carbon and can therefore also be abbreviated with $Co_3O_4$-L1/C;

RT room temperature, it is used synonymously with the expression ambient temperature;

TEA triethylamine;

"wt %", "% by weight" and "weight-%" are used synonymously and mean percent by weight.

SUMMARY OF THE INVENTION

Subject of the invention is a method for the preparation of an alkylated, fluoro alkylated, chloro alkylated or fluorochloro alkylated compound ALKYLCOMPSUBST with heterogeneous catalysis by a reaction of a compound COMPSUBST with an alkylating agent ALKHAL in the presence of a catalyst CAT;

ALKHAL is a compound of formula (III);

R3-X  (III)

wherein

X is Br or I;

R3 is $C_{1-20}$ alkyl;

wherein the $C_{1-20}$ alkyl residue R3 of ALKHAL is either unsubstituted, or at least one hydrogen residue of the $C_{1-20}$ alkyl residue R3 of ALKHAL is substituted by F or Cl;

CAT is Co-L1/C;

L1 is 1,10-phenanthroline;

COMPSUBST is selected from the group consisting of a compound COMPSUBST-I, compound of formula (II), compound of formula (IV), polystyrene, ethene and ethine;

wherein

COMPSUBST-I is a ring RINGA or is a RINGA condensed with a ring RINGB;

RINGA is a 5 or 6 membered carbocyclic or heterocyclic ring, when RINGA is a heterocyclic ring, then RINGA has 1, 2 or 3 identical or different endocyclic heteroatoms independently from each other selected from the group consisting of N, O and S;

when RINGA is a 5 membered ring, then RINGA is unsubstituted or substituted by 1, 2, 3 or 4 identical or different substitutents, when RINGA is a 6 membered ring then RINGA is unsubstituted or substituted by 1, 2, 3, 4 or 5 identical or different substitutents, any of said substitutents of RINGA is independently from any other of said substitutent of RINGA selected from the group consisting of $C_{1-10}$ alkyl, $C_{3-8}$ cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, $S(O)_2R50$, CH=C(H)R28,

C≡C—R24, benzyl, phenyl and naphthyl;

RINGB is a 5 or 6 membered carbocyclic or heterocyclic ring, resulting in a bicyclic having 8, 9 or 10 ring members in total, when RINGB is a heterocyclic ring, then RINGB contains 1, 2 or 3 identical or different endocyclic heteroatoms independently from each other selected from the group consisting of N, O and S;

RINGB is unsubstituted or substituted with 1, 2 or 3 identical or different substituents in case of RINGB being a 5 membered ring, with 1, 2, 3 or 4 identical or different substituents in case of RINGB being a 6 membered ring, which identical or different substitutents are independently from each other selected from the group consisting of $C_{1-10}$ alkyl, $C_{3-8}$ cycloalkyl, $C_{1-4}$ alkoxy, OH, N(R17)R18, CN, NH—OH, NO, $NO_2$, F, Cl, Br, I, $CF_3$, $(CH_2)_n$—C(O)Y2, $S(O)_2R51$, CH=C(H)R38,

C≡C—R34, benzyl, phenyl and naphthyl;

any of said $C_{1-10}$ alkyl substitutent of RINGA or RINGB is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;

any of said benzyl, phenyl and naphthyl substitutent of RINGA or RINGB is independently from each other unsubstituted or substituted with 1, 2, 3, 4 or 5 identical or different substituents selected from the group consisting of halogen, $C_{1-4}$ alkoxy, $NO_2$ and CN;

m and n are identical or different and independently from each other an integer from 0 to 10;

wherein the compound of formula (II) and the compound of formula (IV) being

(II)

(IV)

R40 and R41 are identical or different and independently from each other selected from the group consisting of —(CH$_2$)$_q$—C(O)R13 and —CN;

R42 is selected from the group consisting of —(CH$_2$)$_q$—C(O)R13, —CN and R13;

q is independently an integer from 0 to 10;

wherein the ethene being unsubstituted or substituted by 1, 2 or 3 substitutents selected from the group consisting of C$_{1-10}$ alkyl, C$_{3-8}$ cycloalkyl, C$_{1-4}$ alkoxy, N(R10)R11, CN, NO, NO$_2$, F, Cl, Br, I, CF$_3$, (CH$_2$)$_p$—C(O)Y1, S(O)$_2$R50, CH=C(H)R28,

C≡C—R24, benzyl, phenyl and naphthyl;

the ethine being unsubstituted or substituted by 1 substitutent selected from the group consisting of C$_{1-10}$ alkyl, C$_{3-8}$ cycloalkyl, C$_{1-4}$ alkoxy, N(R10)R11, CN, NO, NO$_2$, F, Cl, Br, I, CF$_3$, (CH$_2$)$_p$—C(O)Y1, S(O)$_2$R50, CH=C(H)R28,

C≡C—R24, benzyl, phenyl and naphthyl;

p is independently an integer from 0 to 10;

any of the R24, R34, R28 and R38 are identical or different and independently from each other selected from the group consisting of H, C$_{1-10}$ alkyl, C(R25)(R26)-O—R27;

any of the R25, R26 and R27 are identical or different and independently from each other selected from the group consisting of H and C$_{1-10}$ alkyl;

any of the R50 and R51 are identical or different and independently from each other selected from the group consisting of OH, C$_{1-6}$ alkyl and C$_{1-6}$ alkoxy;

any of the Y1, Y2 and R13 are identical or different and independently selected from the group consisting of H, OH, C(R14)(R15)R16, C$_{1-6}$ alkyl, O—C$_{1-6}$ alkyl, phenyl, benzyl, O-phenyl, O—C$_{1-6}$ alkylen-O—C$_{1-6}$ alkyl and N(R19)R20;

any of the R14, R15 and R16 are identical or different and independently from each other selected from the group consisting of H, F, Cl and Br;

any of the R10, R11, R17, R18, R19 and R20 are identical or different and are independently from each other H or C$_{1-6}$ alkyl, or R10 and R11, R17 and R18 or R19 and R20 represent together tetramethylene or pentamethylene.

DETAILED DESCRIPTION OF THE INVENTION

Preferably X is Br.

Preferably, when RINGA is a heterocyclic ring, then RINGA has 1, 2 or 3 identical or different endocyclic heteroatoms independently from each other selected from the group consisting of N and S.

Preferably, when RINGB is a heterocyclic ring, then RINGB contains 1, 2 or 3 identical or different endocyclic heteroatoms independently from each other selected from the group consisting of N and S.

Preferably, RINGA is an aromatic ring.

Preferably, RINGB is an aromatic ring.

More preferably, RINGA and RINGB are aromatic rings.

Preferably, COMPSUBST is selected from the group consisting of COMPSUBST-I,

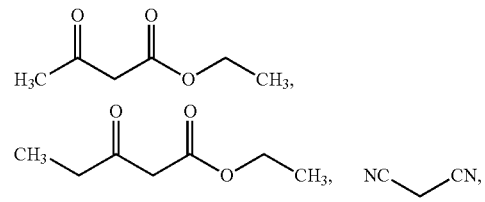

polystyrene, ethene and ethine;

wherein COMPSUBST-I, ethene and the ethine are as defined herein, also with all their embodiments.

In one embodiment, COMPSUBST-I is RINGA or is RINGA condensed with RINGB and is selected from the group consisting of

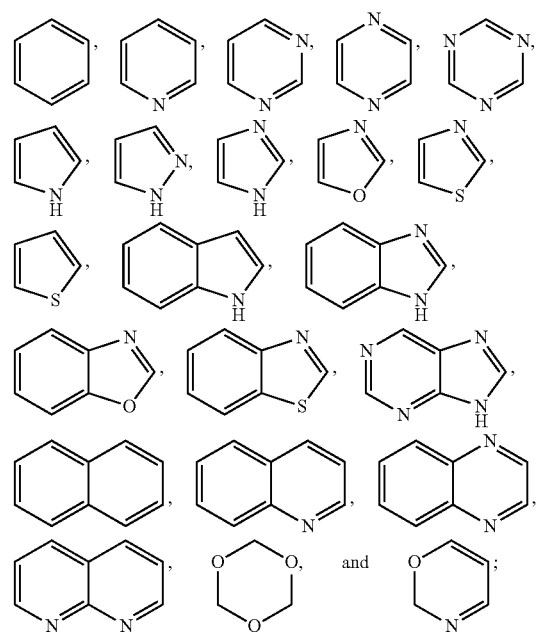

preferably, COMPSUBST-I is RINGA or is RINGA condensed with RINGB and is selected from the group consisting of

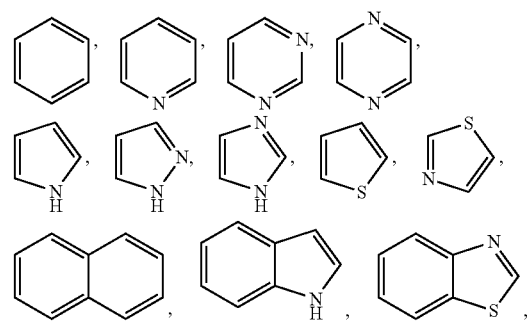

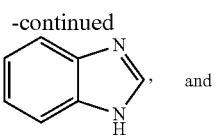

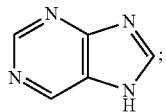

more preferably, COMPSUBST-I is RINGA or is RINGA condensed with RINGB and is selected from the group consisting of

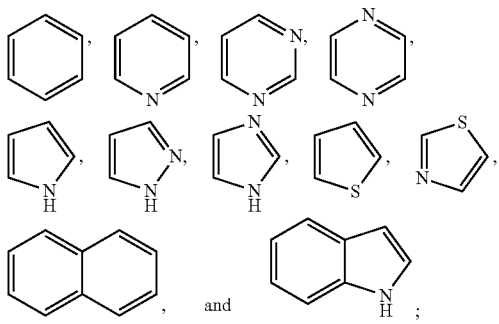

even more preferably, COMPSUBST-I is RINGA or is RINGA condensed with RINGB and is selected from the group consisting of

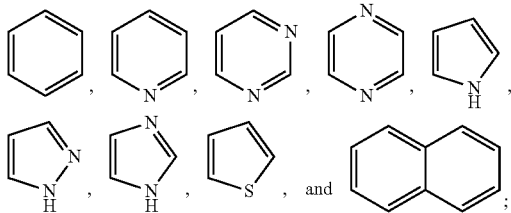

especially, COMPSUBST-I is RINGA and is selected from the group consisting of

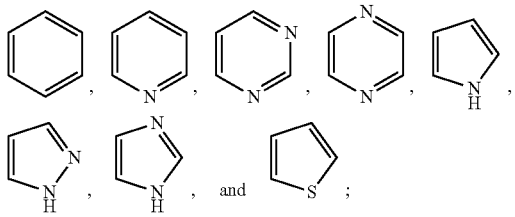

more especially, COMPSUBST-I is RINGA and is selected from the group consisting of

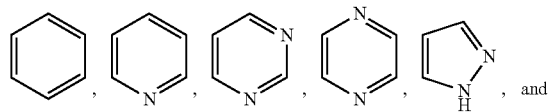

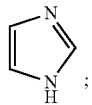

with RINGA or RINGA condensed with RINGB being unsubstituted or substituted
- by 1, 2, 3 or 4 in case of RINGA being a monocyclic compound with 5 endocyclic atoms,
- by 1, 2, 3, 4 or 5 in case of RINGA being a monocyclic compound with 6 endocyclic atoms,
- by 1, 2, 3, 4, 5 or 6 in case of RINGA condensed with RINGB being a bicyclic compound wherein a 5-membered and a 6-membered ring are ortho-fused,
- by 1, 2, 3, 4, 5, 6 or 7 in case of RINGA condensed with RINGB being a bicyclic compound wherein two 6-membered rings are ortho-fused,
- identical or different substituents independently from each other selected from the group consisting of $C_{1-10}$ alkyl, $C_{3-8}$ cycloalkyl, $C_{1-4}$ alkoxy, OH, C(H)=O, N(R10)R11, CN, NH—OH, NO, $NO_2$, F, Cl, Br, I, $CF_3$, $(CH_2)_m$—C(O)Y1, $S(O)_2$R50, CH=C(H)R28,

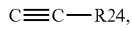

benzyl, phenyl and naphthyl;
said $C_{1-10}$alkyl substitutent is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;
said benzyl, phenyl and naphthyl substitutent is independently from each other unsubstituted or substituted with 1, 2, 3, 4 or 5 identical or different substituents selected from the group consisting of halogen, $C_{1-4}$ alkoxy, $NO_2$ and CN;
wherein
R10 and R11 are identical or different and are independently from each other H or $C_{1-6}$ alkyl or R10 and R11 represent together a tetramethylene or a pentamethylene group;
R24 and R28 are identical or different and are independently from each other OH, $C_{1-10}$ alkyl, C(R25)(R26)-O—R27, with R25, R26 and R27 being identical or different and independently from each other being H or $C_{1-10}$ alkyl;
R50 is OH, $C_{1-6}$ alkyl or $C_{1-6}$ alkoxy;
Y1 is H, OH, C (R14) (R15) R16, $C_{1-6}$ alkyl, O—$C_{1-6}$, phenyl, benzyl, O-phenyl, O—$C_{1-6}$ alkylen-O—$C_{1-6}$ alkyl or N (R19) R20 with R14, R15, R16 being identical or different and independently from each other H, F, Cl or Br;
R19 and R20 being identical or different and are independently from each other H or $C_{1-6}$ alkyl or R19 and R20 represent together a tetramethylene or a pentamethylene group; and
m is independently an integer from 0 to 10.
Herein preferably at each occurrence, m, n, p and q are identical or different and independently from each other an integer 0, 1, 2, 3, 4, 5, 6, 7, 8, 9 or 10;
more preferably at each occurrence, m, n, p and q are identical or different and independently from each other an integer from 0 to 4 and in particular 0, 1, 2, 3 or 4;

even more preferably at each occurrence, m, n, p and q are independently 0 or 4.

In a preferred embodiment at each occurrence, Y1, Y2 and R13 are identical or different and independently from each other selected from the group consisting of H, OH, C(R14)(R15)R16, $C_{2-6}$ alkyl, O—$C_{1-6}$ alkyl, phenyl, benzyl, O-phenyl, O—$C_{1-6}$ alkylen-O—$C_{1-6}$ alkyl and N(R19)R20;

more preferably at each occurrence, Y1, Y2 and R13 are identical or different and independently from each other selected from the group consisting of H, OH, $C_{1-2}$ alkyl, and O—$C_{1-2}$ alkyl.

More preferably, RINGA or RINGA condensed with RINGB is unsubstituted or substituted
- by 1, 2 or 3 in case of RINGA being a monocyclic compound with 5 endocyclic atoms,
- by 1, 2, 3, 4 or 5 in case of RINGA being a monocyclic compound with 6 endocyclic atoms,
- by 1, 2, 3, 4 or 5 in case of RINGA condensed with RINGB being a bicyclic compound wherein a 5-membered and a 6-membered ring are ortho-fused,
- by 1, 2, 3 or 4 in case of RINGA condensed with RINGB being a bicyclic compound wherein two 6-membered rings are ortho-fused,
- identical or different substituents independently from each other selected from the group consisting of $C_{1-4}$ alkyl, $C_{1-4}$ alkoxy, OH, C(H)=O, N(R10)R11, CN, F, Cl, Br, $CF_3$, $(CH_2)_m$—C(O)Y1, and $S(O)_2R50$;

said $C_{1-4}$ alkyl substitutent is unsubstituted or substituted with 1, 2 or 3 identical or different substituents selected from the group consisting of halogen;

with R10, R11, Y1 and R50 as defined above, also with all their embodiments.

In one embodiment, COMPSUBST is selected from the group consisting of benzene, pyrazole,

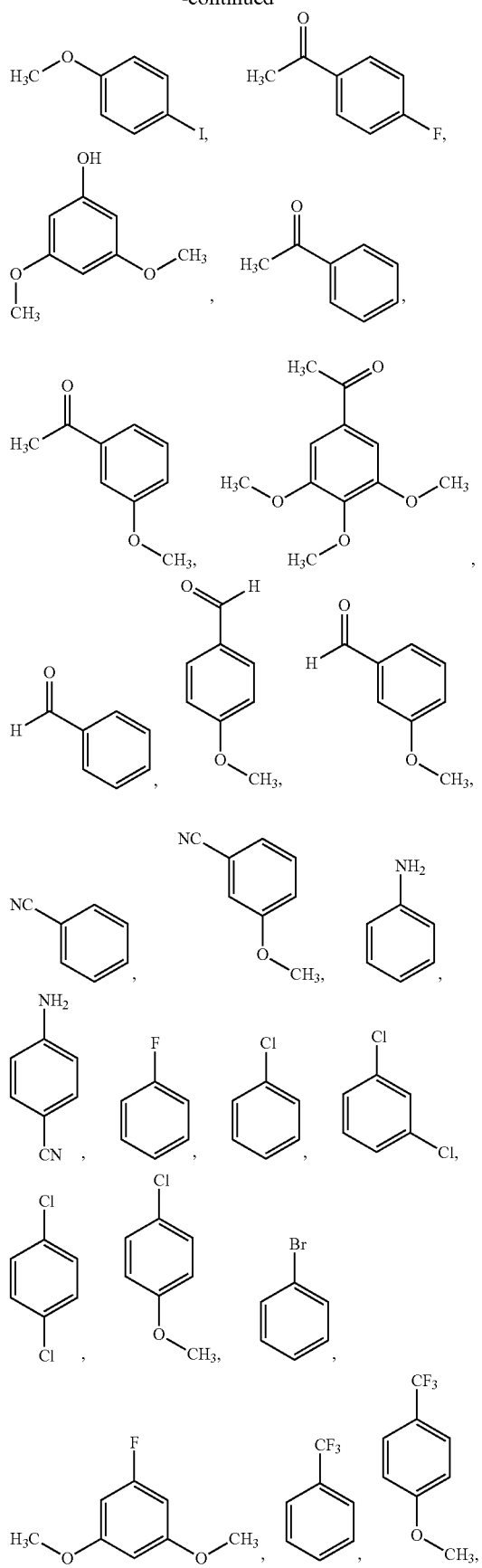

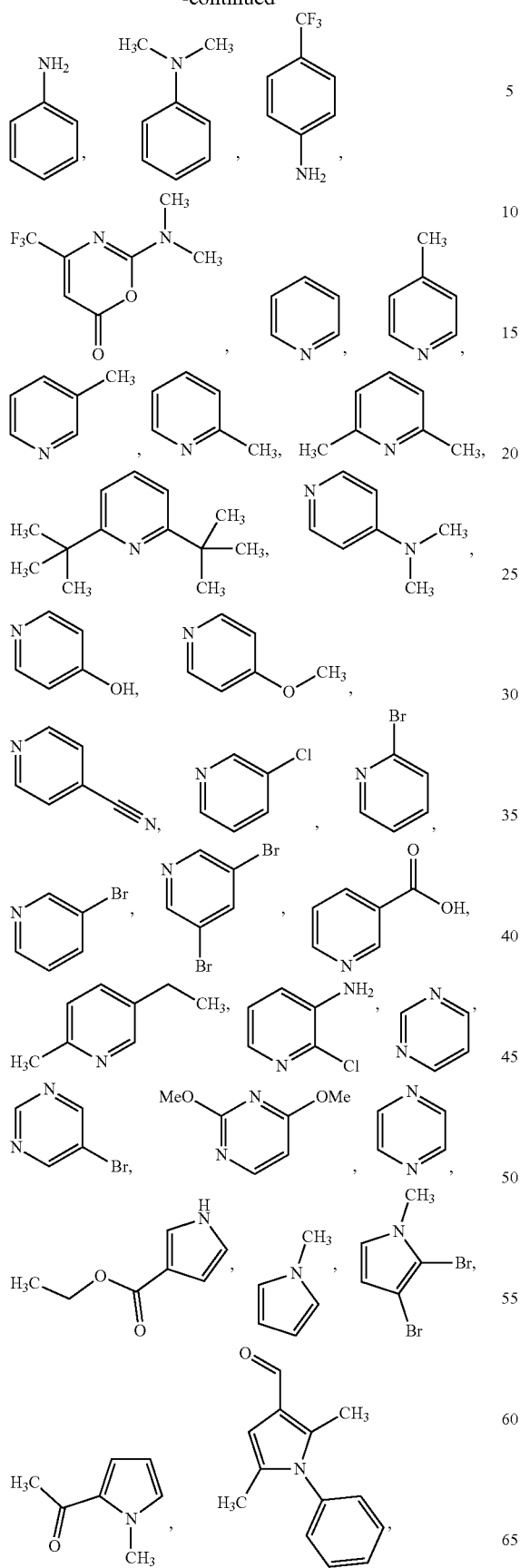
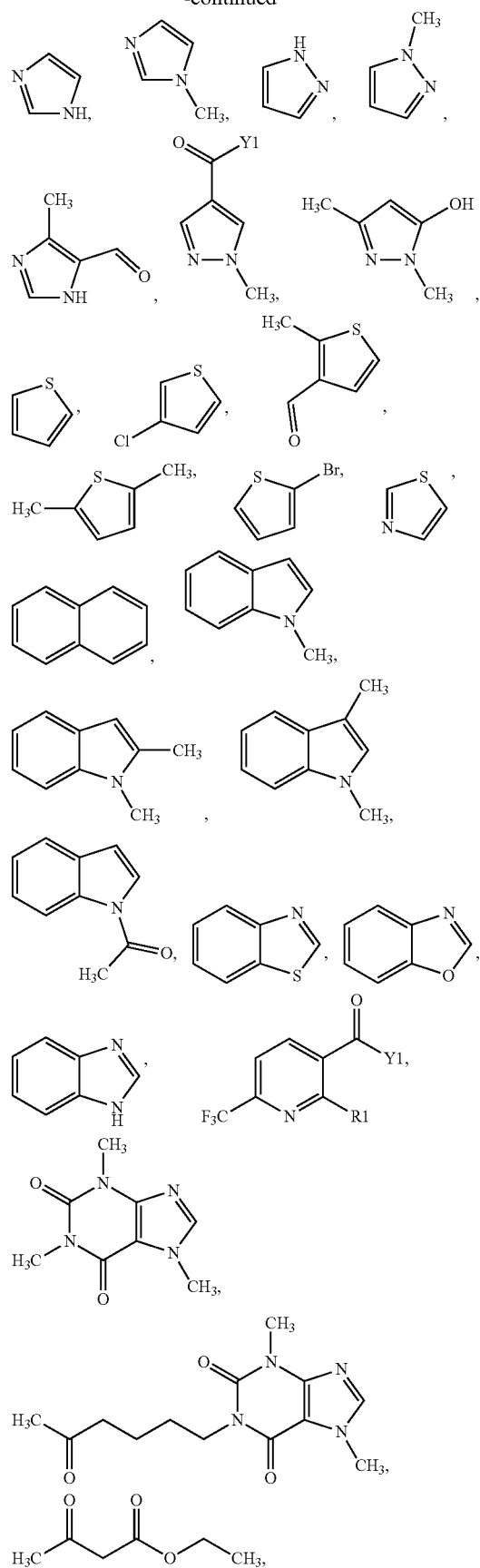

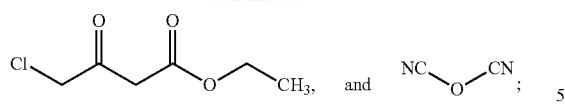

wherein

R1 is selected from the group consisting of $C_{1-10}$alkyl, $C_{3-8}$ cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, $S(O)_2$R50, CH=C(H)R28,

C≡C—R24, benzyl, phenyl and naphthyl;

Y1, R10, R11, m, R50, R28 and R24 are as defined herein, also with all their embodiments;

preferably, Y1 and R1 independently are $C_{1-6}$ alkyl or O—$C_{1-6}$ alkyl.

In a preferred embodiment, COMPSUBST is selected from the group consisting of

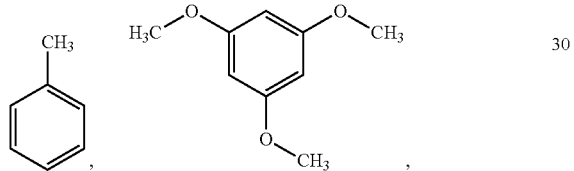

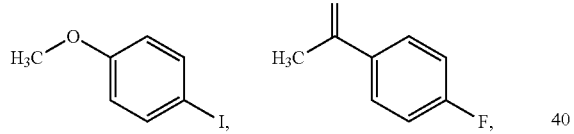

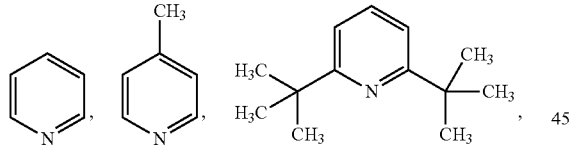

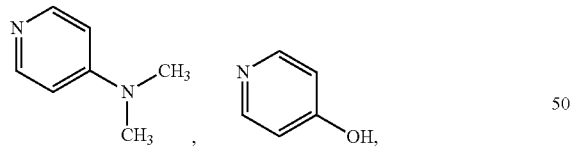

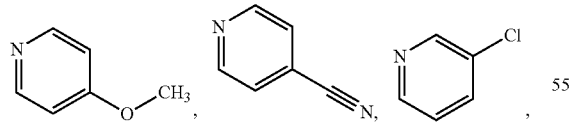

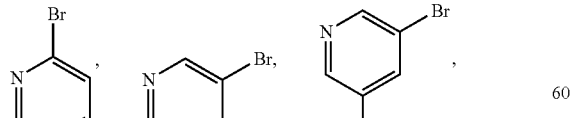

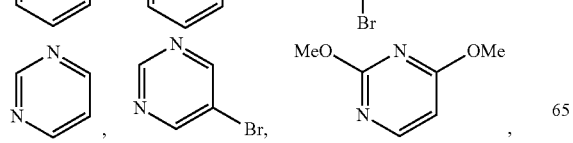

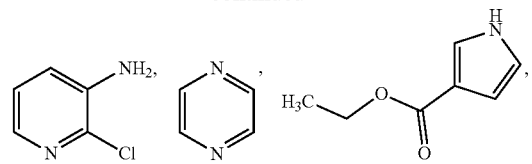

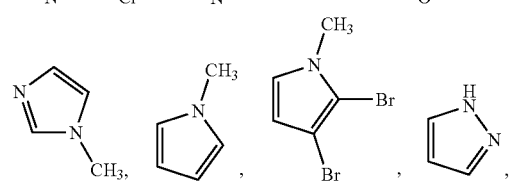

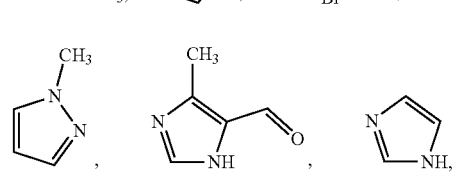

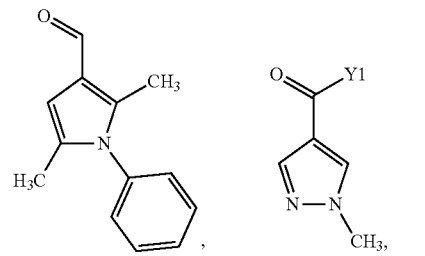

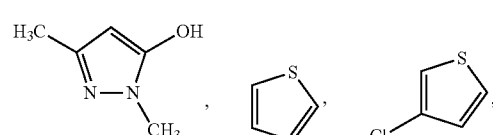

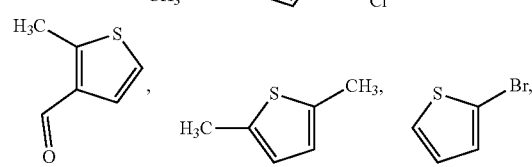

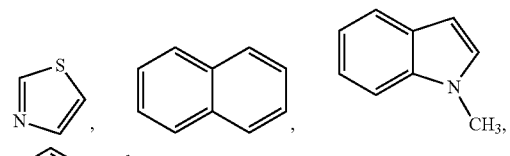

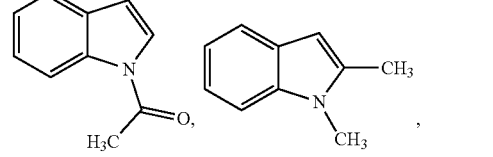

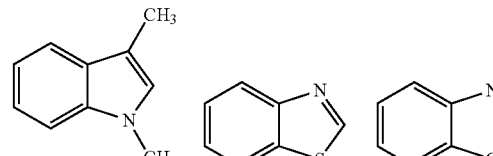

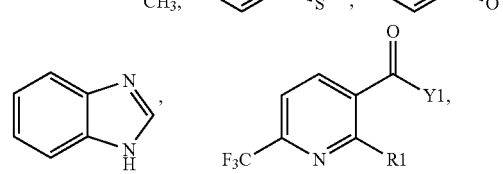

R1 is selected from the group consisting of $C_{1-10}$ alkyl, $C_3$ s cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, $S(O)_2$R50, CH=C(H)R28,

C≡C—R24, benzyl, phenyl and naphthyl;

Y1, R10, R11, m, R50, R28 and R24 are as defined herein, also with all their embodiments;

preferably, Y1 and R1 independently are $C_{1-6}$ alkyl or O—$C_{1-6}$ alkyl.

In a more preferred embodiment, COMPSUBST is selected from the group consisting of -continued

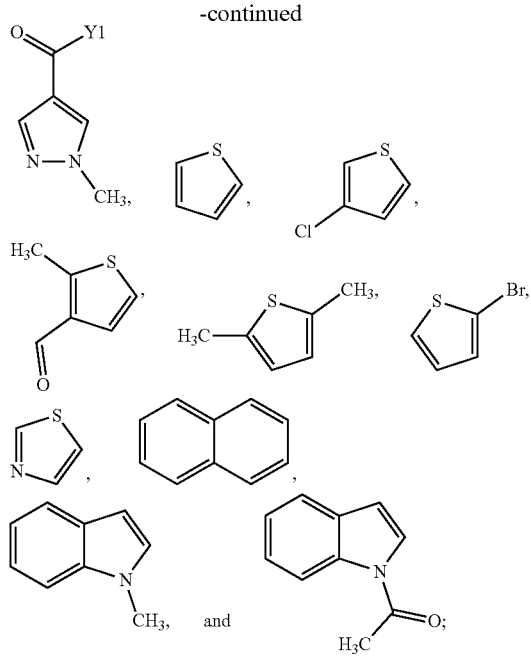

wherein
Y1 is as defined herein, also with all their embodiments; preferably, Y1 is $C_{1-6}$ alkyl or O—$C_{1\text{-}6}$ alkyl;
more preferably, Y1 is methyl, ethyl, methoxy or ethoxy;
even more preferably ethyl or ethoxy.

In an even more preferred embodiment, COMPSUBST is selected from the group consisting of

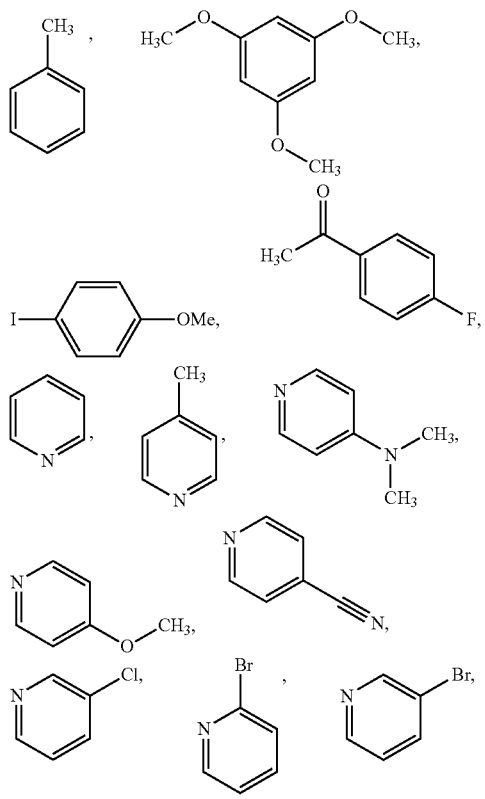

-continued

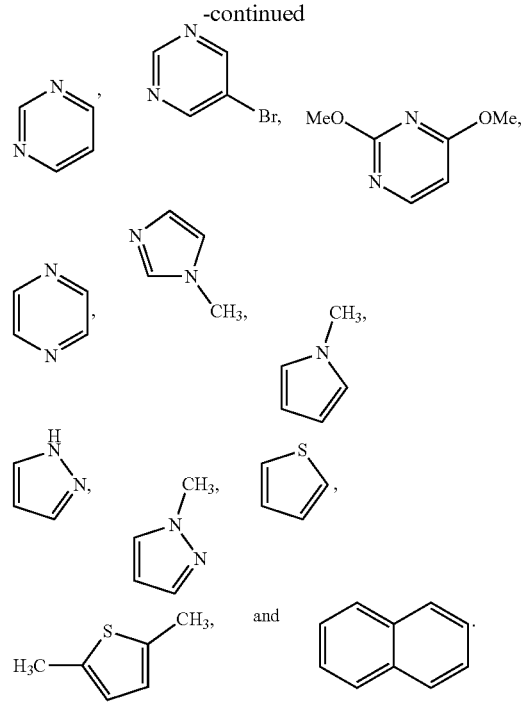

In an especially preferred embodiment, COMPSUBST is selected from the group consisting of

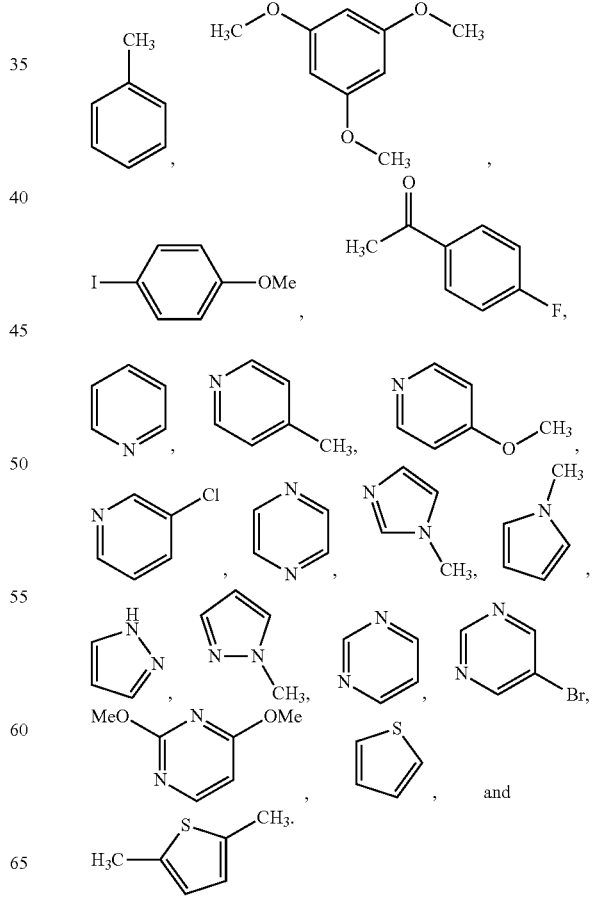

In a more especially preferred embodiment, COMPSUBST is selected from the group consisting of

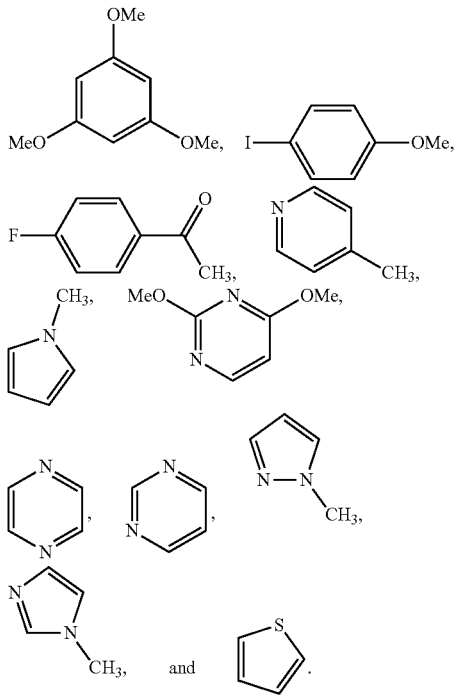

In a further preferred embodiment COMPSUBST is a compound of formula (II), or a compound of formula (IV), wherein als residues are defined as above, also with all their embodiments.

In a further preferred embodiment COMPSUBST is an ethene which is unsubstituted or substituted by 1 or 2 substitutents selected from the group consisting of $C_{1-10}$ alkyl, $C_{3-6}$ cycloalkyl, $C_{1-4}$ alkoxy, N(R10)R11, CN, F, Cl, Br, I, $CF_3$, $(CH_2)_m$—C(O)Y1, $S(O)_2R50$, benzyl, phenyl and naphthyl; or an ethine which is unsubstituted or substituted by 1 substitutent selected from the group consisting of $C_{1-10}$ alkyl, $C_{3-6}$ cycloalkyl, $C_{1-4}$ alkoxy, N(R10)R11, CN, F, Cl, Br, I, $CF_3$, $(CH_2)_m$—C(O)Y1, $S(O)_2R50$, benzyl, phenyl and naphthyl;

more preferably, the ethene is unsubstituted or substituted by 1 or 2 substitutents selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl and phenyl;

more preferably, the ethine being unsubstituted or substituted by 1 substitutent selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl and phenyl;

with R10, R11, m, Y1 and R50 as defined above, also with all their embodiments.

Embodiments of the substituted ethene are propene, ethene-1,1-diyldibenzene and 3,3-dimethylbut-1-ene.

An embodiment of the substituted ethine is 1-octyne.

In a further preferred embodiment COMPSUBST is selected from a compound of formula (V) or a compound of formula (VI)

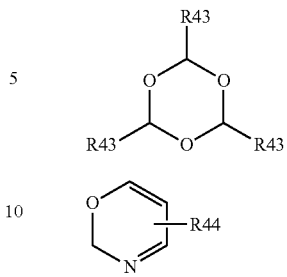

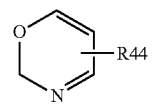

wherein
R43 is H or $CH_3$;
R44 is selected from the group consisting of $C_{1-10}$ alkyl, $C_{1-4}$ alkoxy, OH, N(R10)R11, CN, NO, $NO_2$, F, Cl, Br, I, $CF_3$, $(CH_2)_m$—C(O)Y1, $S(O)_2R50$;
with R10, R11, m, Y1 and R50 as defined above, also with all their embodiments.

Preferably, ALKHAL is a compound of formula (III);

$$R3\text{-}X \quad (III)$$

wherein
X is Br or I; preferably X is Br;
R3 is $C_{1-20}$ alkyl or a $C_{1-20}$ alkyl wherein in the alkyl chain at least one hydrogen is substituted by F or Cl, preferably by F;
more preferably,
R3 is $C_{1-15}$ alkyl or $C_{1-15}$ is alkyl wherein in the alkyl chain at least one hydrogen is substituted by F or Cl, preferably by F;
even more preferably,
R3 is $C_{1-10}$alkyl or $C_{1-10}$ alkyl wherein in the alkyl chain at least one hydrogen is substituted by F or Cl, preferably by F.

Especially, R3 is $C_{1-20}$ alkyl, more especially $C_{1-15}$ alkyl, even more especially $C_{1-10}$ alkyl, wherein all hydrogen atoms are independently substituted by Cl or F, preferably wherein all hydrogen atoms are substituted by F, i.e. an perfluoro alkyl;
in particular, the alkyl is a linear perfluoro alkyl.

Preferably,
X is Br or I;
in one embodiment X is I;
in a preferred embodiment, X is Br;
also with R3 in all its embodiments.

In a preferred embodiment, ALKHAL is a perfluoroalkyl halide, $F_2HC$—Cl or $F_2HC$—Br, preferably ALKHAL is a perfluoroalkyl bromide or iodide, $F_2HC$—Cl or $F_2HC$—Br;
preferably
X is Br or I; and
R3 is perfluoro $C_{1-20}$ alkyl, or
ALKHAL is $F_2HC$—Cl or $F_2HC$—Br;
even more preferably,
X is Br or I; and
R3 is perfluoro $C_{1-15}$ alkyl, or
ALKHAL is $F_2HC$—Cl or $F_2HC$—Br;
especially,
X is Br or I; and
R3 is perfluoro $C_{1-10}$ alkyl, or
ALKHAL is $F_2HC$—Cl or $F_2HC$—Br.

In particular, ALKHAL is selected from the group consisting of $F_{21}C_{10}$—I, $F_{17}C_8$—I, $F_{13}C_6$—I, $F_9C_4$—I, $F_3C$—I, $F_{21}C_{10}$—Br, $F_{17}C_8$—Br, $F_{13}C_6$—Br, $F_9C_4$—Br, $F_3C$—Br, $F_3C$—Cl, $F_2HC$—Cl, and $F_2HC$—Br;

more in particular, ALKHAL is selected from the group consisting of n-$F_{21}C_{10}$—I, n-$F_{17}C_8$—I, n-$F_{13}C_6$—I, n-$F_9C_4$—I, $F_3C$—I, n-$F_{21}C_{10}$—Br, n-$F_{17}C_8$—Br, n-$F_{13}C_6$—Br, n-$F_9C_4$—Br, $F_3C$—Br, $F_3C$—Cl, $F_2HC$—Cl, and $F_2HC$—Br.

In a further preferred embodiment, ALKHAL is selected from the group consisting of $F_{21}C_{10}$—I, $F_{17}C_8$—I, $F_{13}C_6$—I, $F_9C_4$—I, $F_3C$—I, $F_3C$—Br, and $F_2HC$—Br;

in particular, ALKHAL is selected from the group consisting of n-$F_{21}C_{10}$—I, n-$F_{17}C_8$—I, n-$F_{13}C_6$—I, n-$F_9C_4$—I, $F_3C$—I, $F_3C$—Br, and $F_2HC$—Br.

In a further preferred embodiment, ALKHAL is selected from the group consisting of $F_{21}C_{10}$—Br, $F_{17}C_8$—Br, $F_{13}C_6$—Br, $F_9C_4$—Br, $F_3C$—Br, and $F_2HC$—Br;

in particular from the group consisting of n-$F_{21}C_{10}$—Br, n-$F_{17}C_8$—Br, n-$F_{13}C_6$—Br, n-$F_9C_4$—Br, $F_3C$—Br, and $F_2HC$—Br.

The reaction is performed in the presence of or using a catalyst CAT, CAT is Co-L1/C, which is cobalt 1,10-phenanthroline supported on carbon, preferably, CAT is cobalt 1,10-phenanthroline supported on graphene.

Co-L1/C can be prepared according to S1. Catalyst preparation in the Supplementary Information of Westerhaus et al., Nature Chemistry, 2013, 5, 537-543, especially as described schematically in FIG. 1 therein, that is by reacting Co(OAc)$_2$·4 H$_2$O with 1,10-phenantroline and thereby forming a complex Co (phen)$_2$(OAc)$_2$ which is then absorbed on carbon black and kept e.g. at 800° C. for 2 h under argon to provide Co-L1/C, which contains cobalt oxide supported on 1,10-phenantroline/carbon black.

Preferably, the amount of Co in CAT is from 0.1 to 20%, more preferably from 0.5 to 15%, even more preferably from 1 to 12.5%, especially from 2 to 12.5%, the % are % by weight and are based on the total weight of CAT.

Preferably, the amount of Co in the reaction is from 0.001 to 20%, more preferably from 0.01 to 15%, even more preferably from 0.025 to 12.5%, especially from 0.05 to 10%, the % are % by weight % and are based on the weight of ALKHAL.

Preferably, from 1 to 20 mol equivalents, more preferably 1 to 15 mol equivalents, even more preferably from 1 to 10 mol equivalents, of COMPSUBST are used in the reaction, the mol equivalents are based on the molar amount of ALKHAL.

The reaction temperature of the reaction is preferably from 20 to 200° C., more preferably from 20 to 150° C., even more preferably from 40 to 150° C., especially from 70 to 150° C., more especially from 70 to 140° C., even more especially from 100 to 140° C.

The reaction time of the reaction is preferably from 30 min to 72 h, more preferably from 6 h to 60 h, even more preferably from 10 h to 55 h.

Preferably, the reaction is done in the presence of a base BAS, BAS is selected from the group consisting of Cs$_2$CO$_3$, CsHCO$_3$, K$_2$CO$_3$, K$_3$PO$_4$, K$_2$HPO$_4$, KOAc, KOH, Mg(OH)$_2$, TEA, DBU, and HNEt$_2$.

More preferably, BAS is selected from the group consisting of Cs$_2$CO$_3$, K$_2$CO$_3$, K$_3$PO$_4$, K$_2$HPO$_4$, KOAc, KOH, Mg(OH)$_2$, TEA, DBU, and HNEt$_2$.

Even more preferably, BAS is Cs$_2$CO$_3$ or K$_2$CO$_3$; especially, BAS is Cs$_2$CO$_3$.

Preferably, the amount of BAS in the reaction is from 0.1 to 10 mol equivalents, more preferably 0.5 to 5 mol equivalents, even more preferably from 0.75 to 2.5 mol equivalents, the mol equivalents are based on the molar amount of ALKHAL.

Preferably, the reaction is done under inert atmosphere. Preferably, the inert atmosphere is achieved by the use of an inert gas preferably selected from the group consisting of argon, another noble gas, lower boiling alkane, nitrogen and mixtures thereof.

The lower boiling alkane is preferably a $C_{1-3}$ alkane, i.e. methane, ethane or propane.

The reaction can be done in a closed system, or it can be done at a pressure caused by the chosen temperature in a closed system. It is also possible to apply pressure with said inert gas. It is also possible to carry out the reaction at ambient pressure. When ALKHAL is a gaseous substance, e.g. in case of CF$_3$Br, ALKHAL can be used for applying the desired pressure, e.g. when charging ALKHAL.

When pressure is applied, then preferably the reaction is done at a pressure of from 1 to 1000 bar, more preferably of from 1 to 500 bar, even more preferably of from 1 to 200 bar, especially of from 1 to 100 bar, more especially of from 1 to 50 bar.

When ALKHAL is a gaseous substance, e.g. in case of CF$_3$Br, then pressure is applied, then preferably the reaction is done at a pressure of from 2 to 1000 bar, more preferably of from 2 to 500 bar, even more preferably of from 2 to 200 bar, especially of from 2 to 100 bar, more especially of from 2 to 50 bar.

The vapour pressure of CF$_3$Br at ambient temperature is around 14 bar, so when CF$_3$Br is used as ALKHAL, then preferably the reaction is done initially at a pressure of 14 bar or higher.

The reaction can be done by using a solvent SOL. SOL is preferably selected from the group consisting of alkanes, chlorinated alkanes, ketones, ethers, esters, aliphatic nitrils, aliphatic amides, sulfoxides, and mixtures thereof.

More preferably SOL is selected from the group consisting of $C_{5-8}$ alkane, $C_5$-$C_{10}$ cycloalkane, chlorinated $C_{1-8}$ alkane, acetone, methylethylketone (MEK), diethylketone, methyl tert-butyl ether (MTBE), tetrahydrofuran (THF), methyltetrahydrofuran, ethylacetate, butylacetate, valeronitril, acetonitrile, dimethylformamide (DMF), dimethylacetamide, N-methylpyrrolidone (NMP), dimethylsulfoxide (DMSO), dioxaneisopropanol, and mixtures thereof.

Even more preferably, SOL is selected from the group consisting of acetone, MEK, heptane, cyclohexane, DMSO, dichloromethane, ethylacetate, dimethylacetamide, DMF, dioxane, THF, isopropanol, NMP, and mixtures thereof.

Especially, SOL is acetone or methylethylketone; more especially, SOL is acetone.

It is also possible to use COMPSUBST simultaneously as substrate and as solvent.

As an alternative, the reaction can also be carried out in the absence of a solvent, i.e. "in substance". In this case, preferably COMPSUBST serves as solvent. This procedure is in particular applicable for compounds COMPSUBST being liquid at room temperature or having a low melting point of less than 40° C.

The amount of SOL is preferably from 0.1 to 100 fold, more preferably from 1 to 50 fold, even more preferably from 1 to 25 fold, especially from 1 to 15 fold of the weight of ALKHAL.

After the reaction, ALKYLCOMPSUBST can be isolated by standard methods such as evaporation of volatile components, extraction, washing, drying, concentration, crystallization, chromatography and any combination thereof, which are known per se to the person skilled in the art.

COMPSUBST, CAT, ALKHAL and BAS are commercially available and can be prepared according to known precedures.

In one embodiment, the reaction is done in the presence of a compound COMPSALT;

COMPSALT is selected from the group consisting of NaI, KI, CsI, NaBr, KBr, CsBr, N(R30)(R31)(R32)(R33)I, and N(R30)(R31)(R32)(R33)Br;

R30, R31, R32 and R33 are identical or different and independently from each other selected from the group consisting of H and $C_{1-10}$ alkyl;

preferably, R30, R31, R32 and R33 are identical or different and independently from each other selected from the group consisting of H and $C_{2-6}$ alkyl;

more preferably, COMPSALT is selected from the group consisting of NaI, $(n-Bu)_4NI$, NaBr, and $(n-Bu)_4NBr$.

The reaction is preferably done in the presence of a compound COMPSALT and X is Br.

EXAMPLES

Yield:

Yield as used herein is given as a molar yield of the product ALKYLCOMPSUBST based on molar amount of ALKHAL and was determined by quantitative GC analysis with hexadecane as internal standard or as NMR yield, if not otherwise stated.

In particular, yield=conversion x selectivity.

Conversion:

Conversion as used herein is calculated from the molar amount of the remaining ALKHAL (e.g. determining quantitative GC analysis with hexadecane as internal standard), in particular conversion denote the amount of ALKHAL which has reacted during the reaction.

Selectivity:

Selectivity denotes the molar amount of the desired product ALKYLCOMPSUBST based on reacted starting material.

Ratio of Isomers and Position of Alkylation:

This ratio was determined by NMR spectroscopy. Selectivity as given herein always refers to the total amount of all isomers and alkylation positions of ALKYLCOMPSUBST, if not otherwise stated.

Preparation of CAT:

Co-L1/C and its preparation is described in Westerhaus et al., Nature Chemistry, 2013, 5, 537-543, especially in FIG. 1 therein, and in the supplementary information to this article, available under DOI: 10.1038/NCHEM.1645, under chapter "S1. Catalyst preparation", which is cited here:

S1. Catalyst preparation Cobalt(II) acetate tetrahydrate (Sigma-Aldrich ≥98%, 126.8 mg, 0.5 mmol) and 1,10-phenanthroline (Sigma-Aldrich, ≥99%, 183.5 mg, 1.0 mmol) (Co:phenanthroline=1:2 molar ratio) were stirred in ethanol (50 mL) for approximately 30 minutes at room temperature. Then, carbon powder (689.7 mg) (VULCAN® XC72R, Cabot Corporation Prod. Code XVC72R; CAS No. 1333-86-4) was added and the whole reaction mixture was refluxed for 4 hours. The reaction mixture was cooled to room temperature and the ethanol was removed in vacuo. The solid sample obtained was dried at 60° C. for 12 hours, after which it was grinded to a fine powder. Then, the grinded powder was transferred into a ceramic crucible and placed in the oven. The oven was evacuated to ca. 5 mbar and then flushed with argon. The oven was heated to 800° C. at the rate of 25° C. per minute, and held at 800° C. for 2 hours under argon atmosphere. After heating was switched off and the oven cooled back to room temperature. During the whole process argon was constantly passed through the oven. Elemental analysis of Co-Phenanthroline/C (wt %): C=92.28, H=0.20, N=2.70, Co=3.05, O=1.32

As Westerhaus et al., Nature Chemistry, 2013, 5, 537-543, discloses on page 540, in the active catalyst system Co3O4-L1/C the particle sizes had a wide size distribution with a fraction of particles of 2 to 10 nm, and particles and agglomerates in the range 20 to 80 nm. Occasionally, even larger structures up to 800 nm were present. The ratio between all cobalt atoms and all nitrogen atoms in the near-surface region was 1:4.7.

Protocol 1: General Procedure 1 "in Substance"

A mixture of the substrate COMPSUBST (20 eq, 40 mmol), ALKHAL (1 eq, 2 mmol), Co-L1/C (preferably 10 mol % Co, 400 mg, 3 wt % Co-L1/C, if not otherwise stated, prepared according to S1. Catalyst preparation in the Supplementary Information of Westerhaus et al., Nature Chemistry, 2013, 5, 537-543) and BAS, preferably $Cs_2CO_3$ (1 eq, 2 mmol, 652 mg), was placed in a thick-walled pyrex tube with a magnetic stirring bar. The gas atmosphere in the pyrex tube was flushed with nitrogen, the tube was closed with a screw cap and heated with stirring for the reaction time as stated, preferably for 24 h, at the reaction temperature as stated, preferably at 130° C. The resulting mixture was cooled to room temperature and diluted with dichloromethane, ether or methanol (10 ml). The solids were removed by centrifugation (3000 rpm, 15 min) or by filtration. The obtained product solution was analyzed by quantitative GC analysis (internal standard hexadecane) or $^{19}F$-NMR analysis using the internal standards 1,2-difluorobenzene or 1,4-difluorobenzene.

Isolation of the products was conducted by pipette column chromatography using FluoroFlash® reverse phase silica gel (Sigma Aldrich No. 00866) and a gradient solvent elution (1. MeOH:$H_2O$ (4:1 v/v, 10 mL) 2. MeOH (100%, 10 mL) 3. acetone (100%, 10 mL) for long chains fluoroalkyl chains (alkyl chain containing 10 or more carbon atoms) or by normal phase silical gel chromatography using silicagel (Sigma Aldrich No. 236802) and a gradient solvent elution (1. n-pentane (100%) 2. pentane:diethylether (1:1 v/v, 10 ml) for fluoroalkyl chains containing less than 10 carbon atoms.

Protocol 2: General Procedure 2 "in Solution"

A mixture of the substrate COMPSUBST (2 eq, 4 mmol), solvent SOL (2 ml), ALKHAL (1 eq, 2 mmol), Co-L1/C (10 mol % Co, 400 mg, 3 wt % Co/C, prepared according to S1. Catalyst preparation in the Supplementary Information of Westerhaus et al., Nature Chemistry, 2013, 5, 537-543) and $Cs_2CO_3$ (2 eq, 4 mmol, 1.3 g) was placed in a thick-walled pyrex tube with a magnetic stirring bar. The gas atmosphere in the pyrex tube was flushed with nitrogen, the tube was closed with a screw cap and heated with stirring for the reaction time as stated, preferably for 24 h, at the reaction temperature as stated, preferably at 130° C. The resulting mixture was cooled to room temperature and diluted with dichloromethane, ether or methanol (10 ml). The solids were removed by centrifugation (3000 rpm, 15 min) or by filtration. The obtained product solution was analyzed by quantitative GC analysis (internal standard hexadecane) or 19F-NMR analysis using the internal standards 1,2-difluorobenzene or 1,4-difluorobenzene.

Isolation of the products was conducted by pipette column chromatography using FluoroFlash® reverse phase silica gel (Sigma Aldrich No. 00866) and a gradient solvent elution (1. MeOH:H2O (4:1 v/v, 10 mL) 2. MeOH (100%, 10 mL) 3. acetone (100%, 10 mL) for long chains fluoroalkyl chains (alkyl chain containing 10 or more carbon atoms) or by normal phase silical gel chromatography using silicagel (Sigma Aldrich No. 236802) and a gradient solvent elution (1. pentane (100%) 2. pentane:diethylether (1:1 v/v, 10 ml) for fluoroalkyl chains containing less than 10 carbon atoms.

Protocol 3: General Procedure 3 "in Substance" with ALKHAL which is Gaseous at Ambient Temperature A mixture of the substrate COMPSUBST (1 eq, 2.5 mmol), Co-L1/C (10 mol %, 0.25 mmol, 0.49 g, 3 wt % Co/C, prepared according to Si. Catalyst preparation in the Supplementary Information of Westerhaus et al., Nature Chemistry, 2013, 5, 537-543), and $Cs_2CO_3$ (1.1 eq, 2.5 mmol, 0.894 g) was placed in a magnetically stirred Parr autoclave (Parr Instruments 4560 series). After replacing the air in the autoclave with nitrogen, ALKHAL gas was used to increase the pressure in the autoclave to 15 bars, the autoclave was sealed and heated at 130° C. for 48 h with stirring. After cooling the reaction mixture to room temperature, the pressure was released from the autoclave, the reaction mixture diluted with 25 ml diethylether and 1,2-difluorobenzene (300 mg) was added as an internal standard. The solids were removed by centrifugation (3000 rpm, 15 min) or filtration. An aliquot was taken for quantitative GC-MS and $^{19}$F-NMR analysis. The filtrate was concentrated under reduced pressure and the product isolated by column chromatography and gradient elution (1. pentane (100%, 10 ml) 2. pentane:diethylether (1:1 v/v, 10 ml)) to give the product ALKYLCOMPSUBST.

Protocol 4: General Procedure 4 "in Solution" with ALKHAL which is Gaseous at Ambient Temperature A mixture of the substrate COMPSUBST (1 eq, 2.5 mmol), Co-L1/C (10 mol %, 0.25 mmol, 0.49 g, 3 wt % Co/C, prepared according to Si. Catalyst preparation in the Supplementary Information of Westerhaus et al., Nature Chemistry, 2013, 5, 537-543), and $Cs_2CO_3$ (1.1 eq, 2.5 mmol, 0.894 g) and 5 ml acetone (dried, Sigma Aldrich No. 1.00299) was placed in a magnetically stirred Parr autoclave (Parr Instruments 4560 series). After replacing the air in the autoclave with nitrogen, ALKHAL gas was used to increase the pressure in the autoclave to 15 bars, the autoclave was sealed and heated at 130° C. for 48 h with stirring. After cooling the reaction mixture to room temperature, the pressure was released from the autoclave, the reaction mixture diluted with 25 ml diethylether and 1,2-difluorobenzene (300 mg) was added as an internal standard. The solids were removed by centrifugation (3000 rpm, 15 min) or filtration. An aliquot was taken for quantitative GC-MS and $^{19}$F-NMR analysis. The filtrate was concentrated under reduced pressure and the product isolated by column chromatography and gradient elution (1. pentane (100%, 10 ml) 2. pentane:diethylether (1:1 v/v, 10 ml)) to give the product ALKYL-COMPSUBST.

Example 1:1,3,5-trimethoxybenzene

A mixture of the 1,3,5-trimethoxybenzene (1 eq, 2.5 mmol, 0.420 g), Co-L1/C (10 mol %, 0.25 mmol, 0.49 g, 3 wt % Co/C, prepared according to S1. Catalyst preparation in the Supplementary Information of Westerhaus et al., Nature Chemistry, 2013, 5, 537-543), and $Cs_2CO_3$ (1.1 eq, 2.5 mmol, 0.894 g) and 5 ml acetone (dried, Sigma Aldrich No. 1.00299) was placed in a magnetically stirred Parr autoclave (Parr Instruments 4560 series). After replacing the air in the autoclave with nitrogen, $CF_3Br$ gas was used to increase the pressure in the autoclave to 15 bars, the autoclave was sealed and heated at 130° C. for 48 h with stirring. After cooling the reaction mixture to room temperature, the pressure was released from the autoclave, the reaction mixture diluted with 25 ml diethylether and 1,2-difluorobenzene (300 mg) was added as an internal standard. The solids were removed by centrifugation (3000 rpm, 15 min) or filtration. An aliquot was taken for quantitative GC-MS and $^{19}$F-NMR analysis. The filtrate was concentrated under reduced pressure and the product isolated by column chromatography and gradient elution (1. pentane (100%, 10 ml) 2. pentane:diethylether (1:1 v/v, 10 ml)) to give 1,3,5-trimethoxy-2-(trifluoromethyl)benzene (1.5 mmol, 343 mg, 58% yield) and 1,3,5-trimethoxy-2,4-bis(trifluoromethyl)benzene (1.1 mmol, 338 mg, 42% yield) based on the substrate 1,3,5-trimethoxybenzene. The identity of the products was confirmed using HRMS EI (m/z): [M]+ calcd for C10H11F3O3: 236.06603; found: 236.06621 and for C11H10F6O: 304.05341; found: 304.05351.

Example 2

BAS was $Cs_2CO_3$.

Conversion, selectivity and yield are based on the consumption of the respective limiting reagent. In the case of the protocol 1 (neat) the starting material is solvent as well, hence the fluoroalkyl reagent is limiting and the yields are based on it.

In Table 1 and Table 2 the following abbreviations are used:
ac aceton
CONV conversion
PROT protocol
SEL selectivity
SOL solvent
T reaction temperature
t reaction time
ALKHAL has a linear chain, if not otherwise stated.

TABLE 1

| Entry | PROT | COMPSUBST | ALKHAL | ALKYLCOMPSUBST |
|---|---|---|---|---|
| 1 | 4 | 1,3,5-trimethoxybenzene | $CF_3Br$ | 1,3,5-trimethoxy-2-(trifluoromethyl)benzene |
| 2 | 4 | 1,3,5-trimethoxybenzene | $CF_3Br$ | 1,3,5-trimethoxy-2-(trifluoromethyl)benzene |

TABLE 1-continued

| Entry | PROT | COMPSUBST | ALKHAL | ALKYLCOMPSUBST |
|---|---|---|---|---|
| 3 | 4 | 1,3,5-trimethoxybenzene | CF$_3$Br | 1,3,5-trimethoxy-2,4-bis(trifluoromethyl)benzene |
| 4 | 3 | 1,3,5-trimethoxybenzene | CF$_3$Br | 1,3,5-trimethoxy-2-(trifluoromethyl)benzene |
| 5 | 3 | 1-iodo-4-methoxybenzene | CF$_3$Br | 1-iodo-4-methoxy-3-(trifluoromethyl)benzene |
| 6 | 3 | 1-(4-fluorophenyl)ethanone | CF$_3$Br | 1-(4-fluoro-2-(trifluoromethyl)phenyl)ethanone |
| 7 | 1 | 4-methylpyridine | C$_{10}$F$_{21}$I | 3-(C$_{10}$F$_{21}$)-4-methylpyridine |
| 8 | 1 | 4-methylpyridine | C$_6$F$_{13}$Br | 3-(C$_6$F$_{13}$)-4-methylpyridine |
| 9 | 1 | 1-methylpyrrole | C$_6$F$_{13}$Br | 3-(C$_6$F$_{13}$)-1-methylpyrrole |
| 10 | 1 | 2,4-dimethoxypyrimidine | C$_6$F$_{13}$Br | 5-(C$_6$F$_{13}$)-2,4-dimethoxypyrimidine |
| 11 | 1 | pyrazine | C$_6$F$_{13}$Br | 2-(C$_6$F$_{13}$)pyrazine |
| 12 | 1 | pyrimidine | C$_6$F$_{13}$Br | 5-(C$_6$F$_{13}$)pyrimidine |
| 13 | 1 | 1-methylpyrazole | C$_6$F$_{13}$Br | 4-(C$_6$F$_{13}$)-1-methylpyrazole |

TABLE 1-continued

| Entry | PROT | COMPSUBST | ALKHAL | ALKYLCOMPSUBST |
|---|---|---|---|---|
| 14 | 1 | 1-methylimidazole | $C_6F_{13}Br$ | 2-($C_6F_{13}$)-1-methylimidazole |
| 15 | 1 | thiophene | $C_6F_{13}Br$ | 2-($C_6F_{13}$)-thiophene |

TABLE 2

| Entry | SOL | T | t | CONV | SEL | yield |
|---|---|---|---|---|---|---|
| 1 | ac | 130 | 16 | 92% | 90% | 82.5% |
| 2 | ac | 130 | 48 | 100% | 58% | 58% |
| 3 | ac | 130 | 48 | 100% | 42% | 42% |
| 4 | — | 130 | 40 | 21% | 88% | 18.5% |
| 5 | — | 130 | 40 | 15% | 30% | 4.5% |
| 6 | — | 130 | 20 | 100%[1] | 46% | 46% |
| 7 | — | 120 | 20 | 100%[1] | 60% | 60% |
| 8 | — | 130 | 20 | 93%[1] | 46% | 43% |
| 9 | — | 130 | 20 | 100%[1] | 97% | 97% |
| 10 | — | 130 | 20 | 69%[1] | 23% | 16% |
| 11 | — | 130 | 20 | 89%[1] | 27% | 24% |
| 12 | — | 130 | 20 | 87%[1] | 34% | 30% |
| 13 | — | 130 | 20 | 100%[1] | 39% | 39% |
| 14 | — | 130 | 20 | 100%[1] | 74% | 74% |
| 15 | — | 130 | 20 | 100%[1] | 55% | 55% |

Example 3 gives the entry no.
CS means COMPSUBST.
AH means ALKHAL.
ACS means ALKYLCOMPSUBST.
YD means Yield.
IS means isomer(s).
REM means Remarks; were observations are given and where the analytical methods are stated which were used for determination of structure and yield. GC-MS means gas chromatography combined with mass sepctrometry. NMR was $^{19}$F-NMR The reactions in Table 3 were done according to Protocol 1.

Reaction time was 16 h, except for entry 6, where the reaction time was 20 h.

BAS was $Cs_2CO_3$.
CAT was 5 wt % Co-L1/C.

Any alkyl chain is a linear alkyl chain, if not otherwise stated.

Yield was combined yield of any product or isomer observed.

TABLE 3

| # | CS | AH | ACS | YD [%] | REM |
|---|---|---|---|---|---|
| 1 | cyclohexene | $C_7H_{15}Br$ | $C_7F_{15}$-substituted cyclohexene isomers | 59 | 4 IS, GC-MS, NMR |
| 2 | 3-methyl-1-butene | $C_7H_{15}Br$ | 2-($C_7F_{15}$)-3-methyl-1-butene + 4-methyl-2-($C_7F_{15}$)-2-pentene | 25 | 2 IS, GCMS, NMR |
| 3 | 3-buten-1-ol | $C_7H_{15}Br$ | $C_7F_{15}$-substituted butanol + 4-($C_7F_{15}$)-3-buten-1-ol | 20 | 2 IS |

TABLE 3-continued
| # | CS | AH | ACS | YD [%] | REM |
|---|----|----|-----|--------|-----|
| 4 | 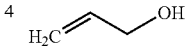 | C$_7$H$_{15}$Br | 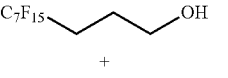 | 11 | 4 IS GCMS NMR |
| 5 | 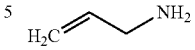 | C$_7$H$_{15}$Br | 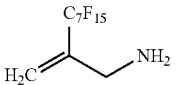 | 67 | 3 IS unsaturated with 50% yield, additional saturated products with 17% yield GCMS NMR |
| 6 | 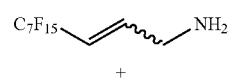 | C$_7$H$_{15}$Br | 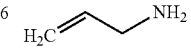 | 67 | 3 IS unsaturated with 50% yield, additional saturated products with 17% yield GCMS NMR |
| 7 | 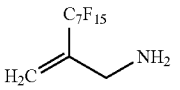 | C$_7$H$_{15}$Br | 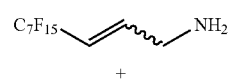 | 26 | 4 IS |
| 8 | 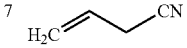 | C$_7$H$_{15}$Br | 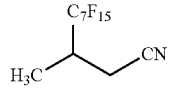 | 39 | GCMS NMR |

TABLE 3-continued

| # | CS | AH | ACS | YD [%] | REM |
|---|---|---|---|---|---|
| 9 | morpholine-cyclohexenyl | C₇H₁₅Br | morpholine-cyclohexenyl with C₆F₁₃ and F substituent | 77 | 1 IS GCMS NMR |
| 10 | HC≡C-CH₂-OH | C₇H₁₅Br | C₇F₁₅-CH=CH-OH + H₂C=C(C₇F₁₅)-OH | 32 | 2 IS GCMS NMR |
| 11 | HC≡C-CH₂-O-CH₃ | C₇H₁₅Br | C₇F₁₅-CH=CH-O-CH₃ + H₂C=C(C₇F₁₅)-O-CH₃ | 37 | 2 IS GCMS NMR |
| 12 | 4-methylpyridine | C₁₀F₂₁I | 4-methyl-3-(C₁₀F₂₁)-pyridine + 4-methyl-2-(C₁₀F₂₁)-pyridine | 23 and 31 | GCMS NMR |
| 13 | 4-methylpyridine | (CF₃)₂CF-I | 4-methyl-2-(CF(CF₃)₂)-pyridine | 4 | GCMS NMR |
| 14 | 4-methylpyridine | I-CH₂-CF₃ | 4-methyl-2-(CH₂CF₃)-pyridine + 4-methyl-3-(CH₂CF₃)-pyridine | 7 and 9 | GCMS NMR |

TABLE 3-continued
| # | CS | AH | ACS | YD [%] | REM |
|---|---|---|---|---|---|
| 15 | 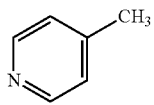 | C₇H₁₅Br | 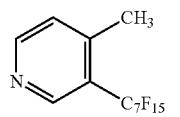 + 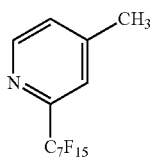 | 23 and 29 | GCMS and NMR |
| 16 | 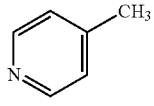 | 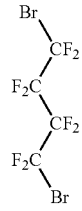 | 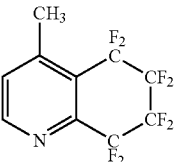 + 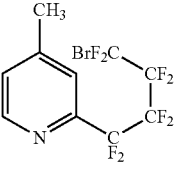 | 23 and 17 | GCMS and NMR |
| 17 | 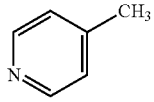 | 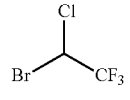 | 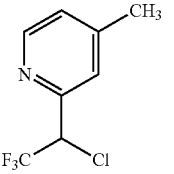 + 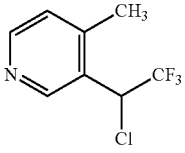 | 6 and 5 | NMR |
| 18 | 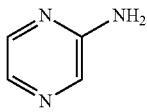 | 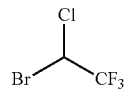 | 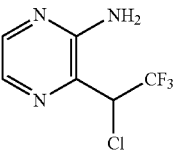 + 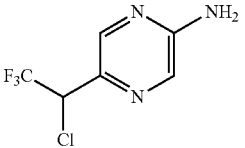 + | 31 and 3 and 1 | GCMS and NMR |

TABLE 3-continued

| # | CS | AH | ACS | YD [%] | REM |
|---|----|----|-----|--------|-----|

[Structure: pyrazine with NH2 and CH(Cl)CF3 substituents]

The invention claimed is:

1. A method for the preparation of fluoro alkylated, chloro alkylated or fluorochloro alkylated compound ALKYL-COMPSUBST with heterogeneous catalysis by a reaction of a compound COMPSUBST with an alkylating agent ALKHAL in the presence of a catalyst CAT;
ALKHAL is a compound of formula (III);

R3-X    (III)

wherein
X is Br or I;
R3 is $C_{1-20}$ alkyl;
wherein the $C_{1-20}$ alkyl residue R3 of ALKHAL is either unsubstituted, or at least one hydrogen residue of the $C_{1-20}$ alkyl residue R3 of ALKHAL is substituted by F or Cl;
CAT is Co-L1/C;
L1 is 1,10-phenanthroline;
COMPSUBST is selected from the group consisting of a compound COMPSUBST-I, compound of formula (II), compound of formula (IV), polystyrene, ethene and ethine;
wherein
COMPSUBST-I is a ring RINGA or is a RINGA condensed with a ring RINGB;
RINGA is a 5 or 6 membered carbocyclic aromatic or heterocyclic aromatic ring,
when RINGA is a heterocyclic ring, then RINGA has 1, 2 or 3 identical or different endocyclic heteroatoms independently from each other selected from the group consisting of N, O and S;
when RINGA is a 5 membered ring, then RINGA is unsubstituted or substituted by 1, 2, 3 or 4 identical or different substitutents,
when RINGA is a 6 membered ring then RINGA is unsubstituted or substituted by 1, 2, 3, 4 or 5 identical or different substitutents,
any of said substitutents of RINGA is independently from any other of said substitutent of RINGA selected from the group consisting of $C_{1-20}$ alkyl, $C_{3-8}$ cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, $S(O)_2$R50,

C≡C—R24,

CH=C(H)R28, benzyl, phenyl and naphthyl;
RINGB is a 5 or 6 membered carbocyclic or heterocyclic ring, resulting in a bicyclic having 8, 9 or 10 ring members in total,
when RINGB is a heterocyclic ring, then RINGB contains 1, 2 or 3 identical or different endocyclic heteroatoms independently from each other selected from the group consisting of N, O and S;

RINGB is unsubstituted or substituted with 1, 2 or 3 identical or different substituents in case of RINGB being a 5 membered ring, with 1, 2, 3 or 4 identical or different substituents in case of RINGB being a 6 membered ring, which identical or different substitutents are independently from each other selected from the group consisting of $C_{1-10}$ alkyl, $C_{3-8}$ cycloalkyl, $C_{1-4}$ alkoxy, OH, N(R17)R18, CN, NH—OH, NO, $NO_2$, F, Cl, Br, I, $CF_3$, $(CH_2)_n$—C(O)Y2, $S(O)_2$R51, CH=C(H)R38,

C≡C—R34, benzyl, phenyl and naphthyl;
any of said $C_{1-10}$ alkyl substitutent of RINGA or RINGB is unsubstituted or substituted with 1, 2, 3, 4 or 5 identical or different substituents selected from the group consisting of halogen, OH, O—C(O)—$C_{1-5}$ alkyl, O—$Ch_{1-10}$ alkyl, S—$Ch_{1-10}$ alkyl, S(O)—$Ch_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;
any of said benzyl, phenyl and naphthyl substitutent of RINGA or RINGB is independently from each other unsubstituted or substituted with 1, 2, 3, 4 or 5 identical or different substituents selected from the group consisting of halogen, $C_{1-4}$ alkoxy, $NO_2$ and CN;
m and n are identical or different and independently from each other an integer from 0 to 10;
wherein
the compound of formula (II) and the compound of formula (IV) being

(II)

(IV)

R40 and R41 are identical or different and independently from each other selected from the group consisting of —$(CH_2)_q$—C(O)R13 and —CN;
R42 is selected from the group consisting of —$(CH_2)_q$—C(O)R13, —CN and R13;
q is independently an integer from 0 to 10;
wherein
the ethene being unsubstituted or substituted by 1, 2 or 3 substitutents selected from the group consisting of $C_{1-10}$ alkyl, $C_{3-8}$ cycloalkyl, $C_{1-4}$ alkoxy, N(R10)R11, CN, NO, $NO_2$, F, Cl,

C≡C—R24,

Br, I, CF₃, (CH₂)ₚ—C(O)Y1, S(O)₂R50, CH═C(H)R28, benzyl, phenyl and naphthyl;
the ethine being unsubstituted or substituted by 1 substitutent selected from the group consisting of $C_{1-10}$ alkyl, $C_{3-8}$ cycloalkyl, $C_{1-4}$ alkoxy, N(R10)R11, CN, NO, NO₂, F, Cl, Br, I, CF₃,

C≡C—R24, (CH₂)ₚ-C(O)Y1, S(O)₂R50, CH═C(H)R28, benzyl, phenyl and naphthyl;
p is independently an integer from 0 to 10;
any of the R24, R34, R28 and R38 are identical or different and independently from each other selected from the group consisting of H, $C_{1-10}$ alkyl, C(R25)(R26)-O-R27;
any of the R25, R26 and R27 are identical or different and independently from each other selected from the group consisting of H and $C_{1-10}$ alkyl;
any of the R50 and R51 are identical or different and independently from each other selected from the group consisting of OH, $C_{1-6}$ alkyl and $C_{1-6}$ alkoxy;
any of the Y1, Y2 and R13 are identical or different and independently selected from the group consisting of H, OH, C(R14)(R15)R16, $C_{1-6}$ alkyl, O—$C_{1-6}$ alkyl, phenyl, benzyl, O—phenyl, O—$C_{1-6}$ alkylen-O—$C_{1-6}$ alkyl and N(R19)R20;
any of the R14, R15 and R16 are identical or different and independently from each other selected from the group consisting of H, F, Cl and Br;
any of the R10, R11, R17, R18, R19 and R20 are identical or different and are independently from each other H or $C_{1-6}$ alkyl, or R10 and R11, R17 and R18 or R19 and R20 represent together tetramethylene or pentamethylene.

2. The method according to claim 1, wherein when RINGA is a heterocyclic ring, then RINGA has 1, 2 or 3 identical or different endocyclic heteroatoms independently from each other selected from the group consisting of N and S.

3. The method according to claim 1, wherein COMP-SUBST-I is RINGA or is RINGA condensed with RINGB and is selected from the group consisting of with RINGA or RINGA condensed with RINGB being unsubstituted or substituted
by 1, 2, 3 or 4 in case of RINGA being a monocyclic compound with 5 endocyclic atoms,
by 1, 2, 3, 4 or 5 in case of RINGA being a monocyclic compound with 6 endocyclic atoms,
by 1, 2, 3, 4, 5 or 6 in case of RINGA condensed with RINGB being a bicyclic compound wherein a 5-membered and a 6-membered ring are ortho-fused,
by 1, 2, 3, 4, 5, 6 or 7 in case of RINGA condensed with RINGB being a bicyclic compound wherein two 6-membered rings are ortho-fused,
identical or different substituents independently from each other selected from the group consisting of $C_{1-10}$ alkyl, $C_{3-8}$ cycloalkyl, $C_{1-4}$ alkoxy, OH, C(H)═O, N(R10)R11, CN, NH—OH, NO, NO₂, F, Cl, Br, I, CF₃, (CH₂)ₘ—C(O)Y1, S(O)₂R50, CH═C(H)R28,

C≡C—R24, benzyl, phenyl and naphthyl;
said $C_{1-10}$ alkyl substitutent is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S-$C_{1-10}$ alkyl, S(O)—$C_{1-10}$ alkyl, S(O₂)—$C_{1-10}$ alkyl, O—$C_{1-6}$ alkylen-O—$C_{1-6}$ alkyl, $C_{3-8}$ cycloalkyl and 1,2,4-triazolyl;
said benzyl, phenyl and naphthyl substitutent is independently from each other unsubstituted or substituted with 1, 2, 3, 4 or 5 identical or different substituents selected from the group consisting of halogen, $C_{1-4}$ alkoxy, NO₂ and CN;
wherein
R10 and R11 are identical or different and are independently from each other H or $C_{1-6}$ alkyl or R10 and R11 represent together a tetramethylene or a pentamethylene group;
R24 and R28 are identical or different and are independently from each other OH, $C_{1-10}$ alkyl, C(R25)(R26)-O-R27, with R25, R26 and R27 being identical or different and independently from each other being H or $C_{1-10}$ alkyl;
R50 is OH, $C_{1-6}$ alkyl or $C_{1-6}$ alkoxy;
Y1 is H, OH, C(R14)(R15)R16, $C_{1-6}$ alkyl, O—CO, phenyl, benzyl, O-phenyl, O—$C_{1-6}$ alkylen-O—$C_{1-6}$ alkyl or N (R19) R20 with R14, R15, R16 being identical or different and independently from each other H, F, Cl or Br;

R19 and R20 being identical or different and are independently from each other H or $C_{1-6}$ alkyl or R19 and R20 represent together a tetramethylene or a pentramethylene group; and m is independently an integer from 0 to 10.

4. The method according to claim 1, wherein m, n, p and q are identical or different and independently from each other 0, 1, 2, 3 or 4.

5. The method according to claim 1, wherein

Y1, Y2 and R13 are identical or different and independently from each other selected from the group consisting of H, OH, C(R14)(R15)R16, $C_{2-6}$ alkyl, O—$C_{1-6}$ alkyl, phenyl, benzyl, O-phenyl, O—$C_{1-6}$ alkylen-O—$C_{1-6}$ alkyl and N(R19)R20.

6. The method according to claim 1, wherein RINGA or RINGA condensed with RINGB is unsubstituted or substituted by 1, 2 or 3 in case of RINGA being a monocyclic compound with 5 endocyclic atoms, by 1, 2, 3, 4 or 5 in case of RINGA being a monocyclic compound with 6 endocyclic atoms, by 1, 2, 3, 4 or 5 in case of RINGA consensed with RINGB being a bicyclic compound wherein a 5-membered and a 6-membered ring are ortho-fused, by 1, 2, 3 or 4 in case of RINGA condensed with RINGB being a bicyclic compound wherein two 6-membered rings are ortho-fused, identical or different substituents independently from each other selected from the group consisting of $C_{1-4}$ alkyl, $C_{1-4}$ alkoxy, OH, C(H)=O, N(R10)R11, CN, F, Cl, Br, $CF_3$, $(CH_2)_m$—C(O)Y1, and $S(O)_2R50$;

said $C_{1-4}$ alkyl substitutent is unsubstituted or substituted with 1, 2 or 3 identical or different substituents selected from the group consisting of halogen.

7. The method according to claim 1, wherein

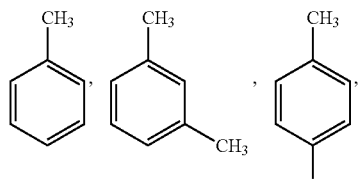

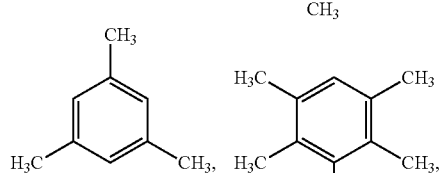

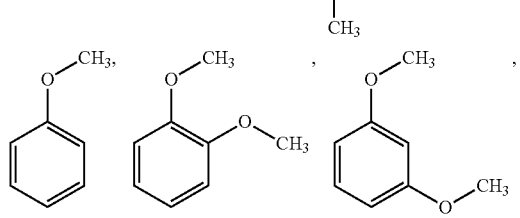

-continued

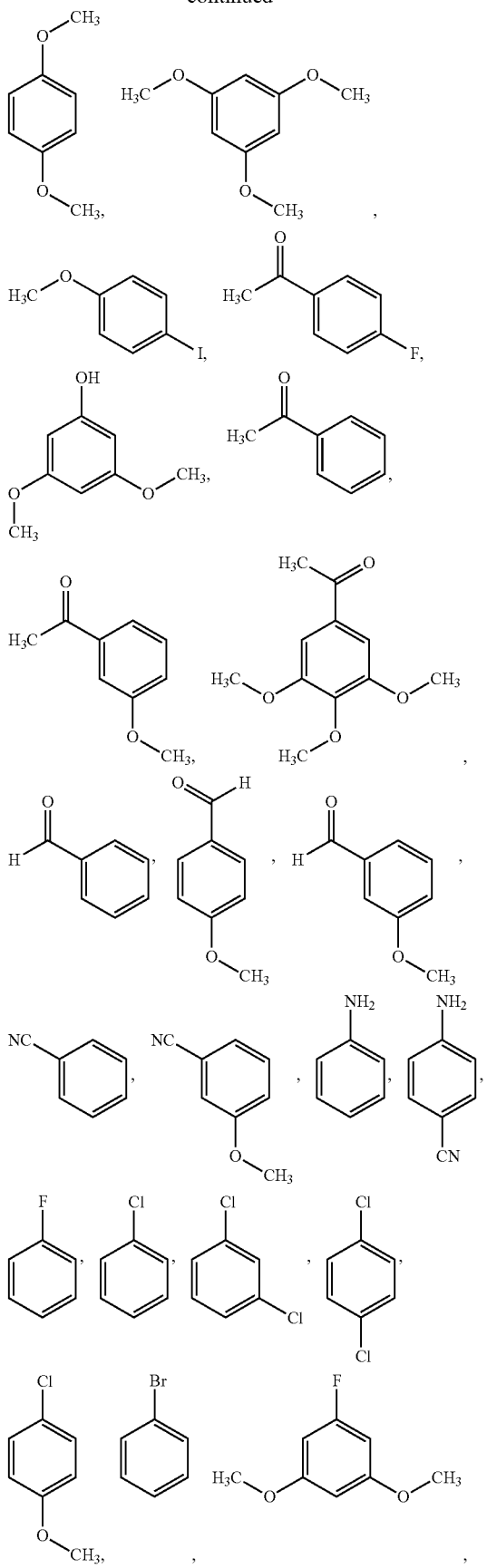

-continued

-continued

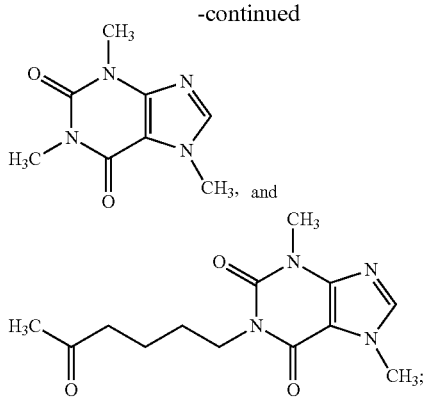

COMPSUBST is selected from the group consisting of benzene, pyrazole,
wherein
R1 is selected from the group consisting of $C_{1-10}$ alkyl, $C_{3-8}$ cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, S(0)2R50,

C≡C—R24,

CH=C(H)R28, benzyl, phenyl and naphthyl;
Y1, R10, R11, m, R50, R28 and R24 are as defined in claim 1.

8. The method according to claim 1, wherein
R3 is $C_{1-20}$ alkyl, wherein all hydrogen atoms are independently substituted by Cl or F.

9. The method according to claim 1, wherein
R3 is $C_{1-20}$ alkyl, wherein all hydrogen atoms are substituted by F.

10. The method according to claim 1, wherein
ALKHAL is selected from the group consisting of $F_{21}C_{10}$—I, $F_{17}C_8$—I, $F_{13}C_6$—I, $F_9C_4$—I, $F_3C$—I, $F_{21}C_{10}$—Br, $F_{17}C_8$—Br, $F_{13}C_6$—Br, $F_9C_4$—Br, $F_3C$—Br, $F_3C$—Cl, $F_2HC$—Cl, and $F_2HC$—Br.

11. The method according to claim 1, wherein Co-L1/C is prepared by reacting $Co(OAc)_2$ 4 $H_2O$ with 1,10-phenantroline and thereby forming a complex Co $(phen)_2(OAc)_2$ which is then absorbed on carbon black and kept at 800° C. for 2 h under argon to provide Co-L1/C.

* * * * *